United States Patent [19]

Buckle

[11] Patent Number: 4,699,995
[45] Date of Patent: Oct. 13, 1987

[54] ARACHIDONIC ACID ANALOGUES, PROCESSES FOR THEIR PREPARATION AND THEIR USE IN MEDICINE

[75] Inventor: Derek R. Buckle, Redhill, England
[73] Assignee: Beecham Group p.l.c., Middlesex, England
[21] Appl. No.: 671,404
[22] Filed: Nov. 14, 1984

[30] Foreign Application Priority Data

Nov. 16, 1983 [GB]  United Kingdom ................ 8330568
May 4, 1984 [GB]  United Kingdom ................ 8411560

[51] Int. Cl.[4] ............................................. C07C 69/76
[52] U.S. Cl. ........................................ 560/61; 560/81; 562/471; 562/489
[58] Field of Search ................... 560/61, 81; 562/471, 562/489; 514/533, 571

[56] References Cited

U.S. PATENT DOCUMENTS 3,748,267  7/1973  Stokes .................................. 252/89

OTHER PUBLICATIONS

Kuchar, M. et al., Cesk. Farm 26 (6), 239–246, 1977.

*Primary Examiner*—Paul J. Killos

*Attorney, Agent, or Firm*—Hopgood, Calimafde, Kalil, Blaustein & Judlowe

[57] ABSTRACT

A compound of formula (I):

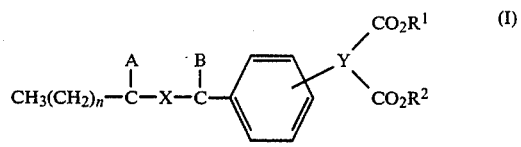

or a salt thereof, in which
Y is a group —$O(CH_2)_m CH<$, —$(CH_2)_m CH<$, or —$CH=C<$ where
m is an integer of from 1 to 5,
n is an integer of from 4 to 12,
each of $R^1$ and $R^2$, which may be the same or different, represents hydrogen or $C_{1-6}$ alkyl,
X represents a double or triple bond, and each of A and B represents hydrogen when X is a double bond, or both A and B are absent when X is a triple bond, is useful in treating allergic diseases.

8 Claims, No Drawings

ARACHIDONIC ACID ANALOGUES, PROCESSES FOR THEIR PREPARATION AND THEIR USE IN MEDICINE

This invention relates to novel arachidonic acid analogues, to processes for preparing them, to pharmaceutical compositions containing them and their use in medicine.

It is known that certain arachidonic acid metabolites can produce harmful effects in man. For example, some prostaglandins and thromboxanes, produced via cyclooxygenation of arachidonic acid, can contribute to inflammation in such diseases as rheumatoid arthritis, and that products produced via lipoxygenation of arachidonic acid, such as the leukotrienes, are implicated in the production of the pathology of asthma and other allergic diseases.

European Published Patent Application No. 0109225 discloses certain arachidonic acid analogues which can inhibit arachidonic acid metabolism by one or both of these metabolic pathways.

We have now discovered a new class of arachidonic acid analogues which can similarly inhibit arachidonic acid metabolism and are thus of value in the prophylaxis and treatment of diseases whose symptoms are controlled by these mediators.

According to the present invention there is provided a compound of formula (I):

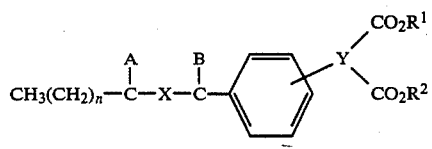

or a salt thereof, in which

Y is a group $-O(CH_2)_mCH<$, $-(CH_2)_mCH<$, or $-CH=CH<$ where m is an integer of from 1 to 5 n is an integer of from 4 to 12 each of $R^1$ and $R^2$, which may be the same or different, represents hydrogen or $C_{1-6}$ alkyl X represents a double or triple bond, and each of A and B represents hydrogen when X is a double bond, or both A and B are absent when X is a triple bond.

When X is a double bond, the hydrocarbon chain containing X may have the (E) or (Z) absolute configuration, preferably (Z).

Similarly, when Y is $-CH=C<$, the

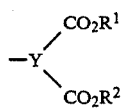

group may have the (E) or (Z) absolute configuration.

The compounds of this invention can exist, therefore, in up to four geometric isomeric forms, and the invention encompasses all geometric isomers of the compounds of formula (I) whether as individual isomers or admixed with each other in any proportion.

The substituents on the aromatic ring may be in the 1,2; 1,3; or 1,4 positions, preferably in the 1,2 or 1,3 positions.

Salts of compounds of formula (I) need not be pharmaceutically acceptable, since they can be used as intermediates to prepare other pharmaceutically acceptable compounds of the invention.

Examples of pharmaceutically acceptable salts include alkali metal and alkaline earth metal salts, such as sodium, potassium and magnesium salts,; and salts with ammonia, organic bases and amino compounds.

Preferably, n is an integer of from 8 to 12.

Preferably, m is 1, 2, or 3.

According to a further aspect of the invention there is provided a process for preparing a compound of the invention which comprises treating a compound of formula (II).

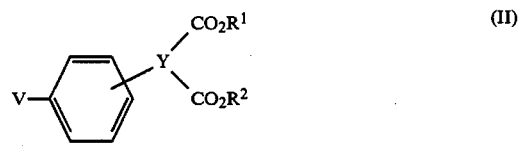

in which Y is as defined with reference to formula (I), each of $R^1$ and $R^2$ are $C_{1-6}$ alkyl, V represents

$-CH^{\ominus}-PPh_3^{\oplus}$ or halogen, preferably bromine or iodine, with a compound of formula (III), $$CH_3(CH_2)_n-W \qquad (III)$$

in which W is

$-CH^{\ominus}-PPh_3^{\oplus}$, $-CH=CH_2$ or $-C\equiv CH$, and, optionally thereafter reducing the carbon-carbon triple bond, when present in the resultant product, to a carbon-carbon double bond, and/or optionally converting the resultant product to the corresponding mono- or dibasic acid with the provisos that (i) when V is

W is $-CH^{\ominus}-PPh_3^{\oplus}$, (ii) when V is $-CH^{\ominus}-PPh^{\oplus}$, W is

and (iii) when V is halogen, W is $-CH=CH_2$ or $-C\equiv CH$

When V is halogen, preferably bromine or iodine and W is $-CH=CH_2$ or $C\equiv CH$, the reaction is preferably carried out by refluxing the reactants in the presence of a palladium (II) salt/triarylphosphine catalyst in a tertiary amine, such as triethylamine, as a diluent and proton sink. A preferred catalyst is palladium acetate/triphenylphosphine, Pd(OAc)$_2$[Ph$_3$P]$_2$.

The resultant compound of the invention may be separated from the reaction mixture by chromatography of the filtered and evaporated reaction mixture.

When V or W is

or —CH$^\ominus$—PPh$_3^\oplus$, the reaction is preferably carried out in a suitable solvent, preferably dimethylsulphoxide or tetrahydrofuran, at ambient temperature and the product purified chromatographically. The reaction will generally produce a mixture of geometrical isomers which can be separated in conventional manner, such as by chromatography, for example on argentated silica gel.

When the resultant compound of the invention formed by reacting compounds of formula (II) and (III) includes a carbon-carbon triple bond, as will occur when W is C≡CH, a further compound of the invention may be formed by reducing the triple bond to a double bond. This reduction may be carried out by conventional literature procedures, preferably by hydrogenation in the presence of a Lindlar catalyst, or other poisoned catalyst such as palladium on barium sulphate. This reduction tends to be stereospecific to the extent that the CH$_3$(CH$_2$)$_n$—W— chain in the resultant compound of the invention has the (Z) configuration.

The resulting compound of the invention in which each of R$^1$ and R$^2$ is C$_{1-6}$ alkyl may be quantitatively hydrolysed with base, for example lithium hydroxide in aqueous tetrahydrofuran, to give a mono- or dibasic acid of formula (I), in which only one of R$^1$ and R$^2$ is hydrogen, or both of R$^1$ and R$^2$ are hydrogen, respectively. In general, treatment with 1 mole equivalent of base will yield a monobasic acid, and 2 mole equivalents will yield a dibasic acid. When Y in formula (I) is —CH=C<, the monobasic acids of formula (I) may have different geometric isomerism, according to whether R$^1$ or R$^2$ is hydrogen.

The intemediate compounds of formula (II) may be prepared in a number of ways, as described hereinafter.

Compounds of formula (II) in which Y is —O(CH$_2$)$_m$CH< and V is

may be prepared by treating an hydroxy benzaldehyde with a bromo-alkanoate ester of formula (IIA)

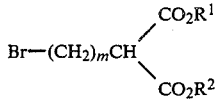

wherein m is as defined in formula (I) and R$^1$ and R$^2$ are each C$_{1-6}$ alkyl, according to the general method disclosed in British Patent Specification No. 1350883.

Compounds of formula (II) in which Y is —O(CH$_2$)$_m$-CH< and V is —CH$^\ominus$—PPh$_3^\oplus$ may be prepared by treating a compound of formula (IIB).

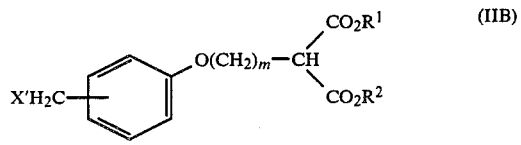

in which m is as defined in formula (I), and R$^1$ and R$^2$ are each C$_{1-6}$ alkyl, and X' is halogen, preferably bromine, with triphenylphosphine to form the phosphonium salt, followed by proton abstraction with a strong base such as n-butyl lithium.

Compounds of formula (IIB) may themselves be prepared by reducing a compound of formula (II) in which Y is —O(CH$_2$)$_m$CH< and V is

to the corresponding alcohol, and subsequently treating the alcohol with a halogenating agent. The reduction is conveniently carried out by sodium borohydride, and a preferred halogenating agent is carbon tetrabromide triphenyl phosphine.

Compounds of formula (II) in which Y is —CH=C< and V is —CH$^\ominus$—PPh$_3^\oplus$ may be prepared by reacting a compound of formula (IID).

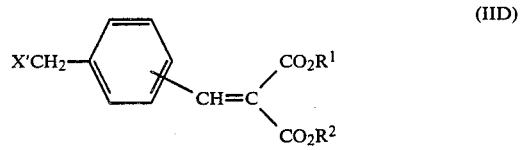

wherein X' is halogen, preferably bromine, with triphenylphosphine, and subsequently treating the resulting compound of formula (IIE).

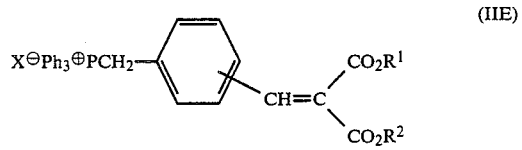

with sodium methylsulphinylmethylide in dimethylsulphoxide.

Compounds of formula (IID) may themselves be prepared in an analogous manner to those of formula (IIB).

Compounds of formula (II) in which V is halogen and Y and R are as defined in formula (II) are either known compunds or can be prepared from known compounds by known methods. For example, a bromobenzaldehyde may be condensed with a dialkyl malonate under standard Knoevenagel conditions (M. S. Newman and D. K. Philips *J. Amer. Chem. Soc.* 81, 3667 (1959)) to give a compound of formula (II) in which V is bromine and Y is

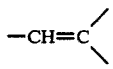

Also, a dibromide of formula (IIF)

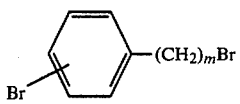

may be coupled with a dialkyl malonate under standard base mediated conditions (F. G. Holliman and F. G. Mann *J. Chem. Soc.* 9, (1960)) to give a compound of formula (II) in which V is bromine and Y is —$(CH_2)_m$—CH<, in which m is as defined in formula (I)

Compounds of formula (II) in which Y is —CH=C< and V is

can be prepared from known compounds by known methods.

The intermediate compounds of formula (III) in which W is

—CH=$CH_2$ or —C≡CH are either known compounds or can be prepared from known compounds by known methods.

The compounds of formula (III) in which W is —CH⊖—$PPh_3^⊕$ may be prepared by reacting the corresponding phosphonium bromide with sodium methylsuphinylmethylide, according to the method described in *J. Org. Chem.*, 28, 1128, 1963 (Greinwald et al), or by reaction with butyl lithium in tetrahydrofuran.

Compounds of the invention may also be prepared by alternative processes, described as follows.

Compunds of formula (I) in which $R_1$ and $R_2$ are each $C_{1-6}$ alkyl and Y is —$O(CH_2)_m$CH< or —$(CH_2)_m$CH< may be prepared by treating a compound of formula (IV),

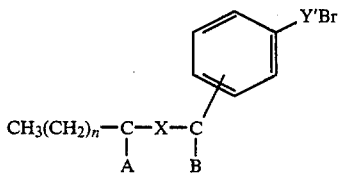

in which n, A,B and X are as defined in formula (I), and Y' is —$O(CH_2)_m$— or —$(CH_2)_m$—, with a malonic diester of formula (V)

in which $R^1$ and $R^2$ are each $C_{1-6}$ alkyl

Compounds of formula (IV) may themselves be prepared by (a) treating a compound of formula (IVA),

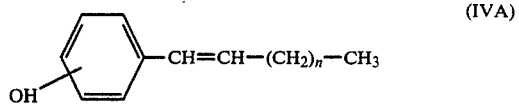

with a compound of formula (IVB),

wherein m and n are as defined in formula (I), or (b) treating a compound of formula (IVC)

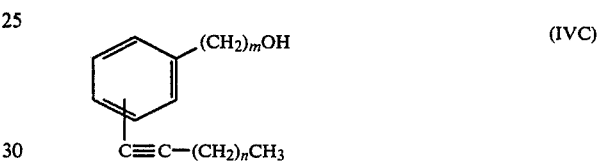

with a mixture of triphenylphosphine and carbon tetrabromide, preferably in dichloromethane.

The reaction between compounds of formulae (IVA) and (IVB) is preferably carried out in a basic medium such as potassium carbonate in butanone.

Compounds of formula (IVA) can themselves be prepared by treating an hydroxy benzaldehyde with a compound of formula (III), in which W is —CH⊖—$PPh_3^⊕$, preferably in a solvent such as dimethylsulphoxide or tetrahydrofuran at ambient temperature.

Compounds of formula (IVC) can be prepared by reducing a compound of formula (VI)

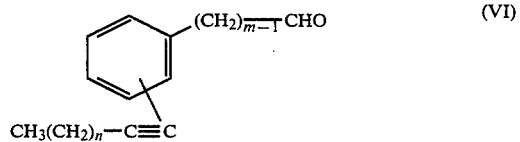

preferably with sodium borohydride or diisobutylaluminium hydride (DIBAL)

Compounds of formula (I) in which $R^1$ and $R^2$ are each $C_{1-6}$ alkyl, Y is —CH=C< and X is a triple bond may be prepared by treating a compound of formula (VI) as defined above, wherein m=1, with a compound of formula (V) as defined above. The reaction is preferably carried out by refluxing the reactants in benzene or toluene as a diluent, and a catalyst such as piperidine/benzoic acid such that the water produced is removed azeotropically.

The compounds of formula (VI) may themselves be prepared by treating a compound of formula (VII).

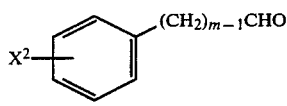 (VII)

in which $X^2$ is bromine or iodide, preferably bromine, with a compound of formula (III) in which W is —C≡CH.

The reaction is preferably carried out by refluxing the reactants in the presence of a palladium (II) salt/triarylphosphine catalyst, as described hereinbefore.

Compounds of formulae (V) and (VII) are either known compounds or can be prepared from known compounds by known methods.

Compounds of formula (I) in which $R^1$ and $R^2$ are each $C_{1-6}$ alkyl and Y is —O(CH$_2$)$_m$CH< may also be prepared by treating a compound of formula (VIII)

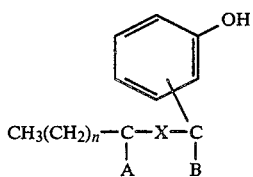 (VIII)

in which n, A, B and X are as defined in formula (I) with a compound of formula (IX)

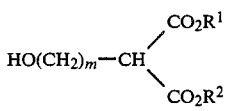 (IX)

in which m, $R_1$ and $R_2$ are as defined in formula (I).

The reaction is preferably carried out in an inert organic solvent such as tetrahydrofuran, in the presence of triphenylphosphine and diethyl azodicarboxylate.

Compounds of formula (VIII) in which X is a triple bond may be prepared using the following reaction schemes

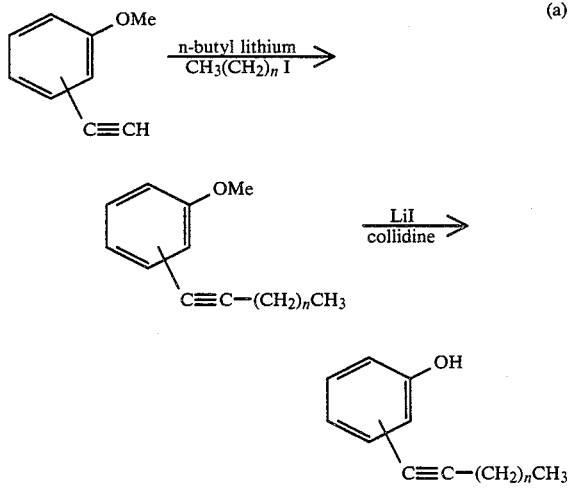

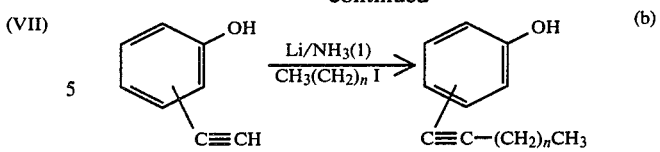 (b)

Reaction scheme (a) is, however, not suitable for those cases in which the generated hydroxyl groups and the appended chain are ortho to each other.

The compounds of formula (I) are active therapeutically, and, accordingly, this invention also provides a pharmaceutical composition comprising a compound of formula (I) as defined above, or a pharmaceutically acceptable salt thereof, and a pharmaceutically acceptable carrier.

A compound of formula (I), or salt thereof, which is active when given by the oral route, may be compounded in the form of syrups, tablets, capsules, pills and the like. Preferably, the composition is in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers solutes to render the solution isotonic with the blood, thickening agents, suspending agents or other pharmaceutically acceptable additives. Such forms will be presented in unit dose form such as ampoules or disposable injection devices or in multidose forms such as a bottle from which the appropriate dose may be withdrawn or a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A compound of general formula (I) or salt thereof, may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 10 mgs via inhalation. The effective dose of compound depends on the particular compound employed, the condition of the patient and on the frequency and route of administration, but in general is in the range of from 0.001 mg/kg/day to 100 mg/kg/day inclusive of the patient's body weight.

Within the above indicated dosage range, no adverse toxicological effects have been observed with the compounds of the invention.

As in common practice, the compositions will usually be accompanied by written or printed directions for use in the medical treatment concerned, in this case as an anti-allergic agent for the prophylaxis and treatment of, for example, asthma, hay fever, rhinitis or allergic eczema.

The invention also provides a method for treating allergic diseases in human and non-human animals, which comprises administering to the sufferer an effective non toxic amount of a compound of formula (I) or a pharmaceutically acceptable salt thereof.

The following Examples illustrate the preparation of compounds of this invention.

EXAMPLE 1

Diethyl 2-(2-bromophenyl)methylene propan-1,3-dioate

A solution of 2-bromobenzaldehyde (45 g) and diethyl malonate (40 g) in dry benzene (125 ml) was treated with benzoic acid (1.5 g) and piperidine (1.75 ml) and refluxed for 17 hours under a Dean and Stark head. A further 0.5 ml of piperidine was then added and the mixture refluxed for a further 7 hours and then cooled. Ether was added and the organic phase was washed with dilute hydrochloric acid, sodium bicarbonate solution and then dried. Evaporation and distillation gave 55.22 g (69%) of pale yellow oil of bp$_{0.2}$ 162°–164° C. (lit bp$_{1.0}$ 178°–181° C., M. S. Newman and D. K. Phillips, *J. Amer. Chem. Soc.*, 81, 3667, [1959]).

EXAMPLE 2

Diethyl 2-(4-bromophenyl)methylene propan-1,3-dioate

The method used was that described in example 1 to give the title compound in 86% yield of bp$_{0.5}$ 147°–152° C., mp 43°–44° C.

Found: C, 51.50, H, 4.38, $C_{14}H_{15}BrO_4$ requires: C, 51.39, H, 4.62%.

EXAMPLE 3

2-(1-Tridecynyl)benzaldehyde

Palladium acetate (96 mg) was added to a deaerated mixture of 2-bromobenzaldehyde (7.40 g, 40 mmol), 1-tridecyne (12.2 g, 68 mmol) and triphenylphosphine (320 mg) in dry triethylamine (160 ml) and the mixture was stirred at 105° C. under a nitrogen atmosphere overnight. After cooling, the precipitated triethylamine hydrobromide was filtered off and the filtrate was evaporated to a crude red oil. Chromatography on silica gel eluting with dichloromethane:petroleum ether [bp 60°–80° C.](1:1) afforded 7.12 g (63%) of the title compound of bp$_{0.05}$ 212° C. (Kugelrohr), M+ 284.2141 ($C_{20}H_{28}O$ requires; 284.2140).

Found: C, 84.31, H, 10.30, $C_{20}H_{28}O$ requires: C, 84.45, H, 9.92%.

The 2,4-dinitrophenylhydrazone had mp (acetic acid) 132° C. Found: C, 67.17, H, 6.84, N, 11.98, $C_{26}H_{32}N_4O_2$ requires: C, 67.22, H, 6.94, N, 12.06%.

EXAMPLE 4

4-(1-octynyl)benzaldehyde

The method as described in example 3 was followed to give the title compound in 52% yield after chromatography on silica eluting with dichloromethane:hexane (1:3). The 2,4-dinitrophenylhydrazone had mp (EtOH) 180°–183° C.

Found, C, 63.31, H, 5.71, N, 13.06, $C_{21}H_{22}N_4O_4.0.5C_2H_5OH$ requires, C, 63.29, H, 6.03, N, 13.42%.

EXAMPLE 5

3-(1-Tridecynyl)benzaldehyde

Reaction of 3-bromobenzaldehyde with 1-tridecyne as described in example 3 gave 85% of the title compound after chromatography on silica, eluting with dichloromethane:petrol (bp 40:60) (1:3) $\nu$max (neat) 2920, 2215, 1705, 1600, 1575, 1465, 1280, 1155, 795, and 680 cm$^{-1}$, $\delta$(CDCl$_3$) 0.86 (3H, distorted t), 0.9–1.7 (18H, m), 2.4(2H, t, J=6 Hz), 7.7–7.9 (4H, m, aromatic), and 10.0 (1H, s, aldehyde). Analysed as the 2,4-dinitrophenylhydrazone m.p. 127° C. (recrystallized from acetic acid). Found, C, 67.27, H, 6.86; N, 12.01, $C_{26}H_{32}N_4O_4$ requires, C, 67.33, H, 6.79, N, 12.08%.

EXAMPLE 6

Diethyl 2-[(1-tridecynyl)phenyl]methylenepropan-1,3-dioate

Reaction of diethyl 2-(2-bromophenyl)methylenepropan-1,3-dioate (6.54 g, 20 mmole, from example 1) with 1-tridecyne (6.1 g, 34 mmole) as described in example 3 gave 5.37 g (63%) of the title compound after chromatography on silica gel eluting with dichloromethane: petroleum ether [bp 60°–80° C.] (1:1). It had, $\nu_{max}$ (film) 1730, 2850, 2920 cm$^{-1}$, $\delta$(CDCl$_3$) 0.84 (3H, distorted t, terminal CH$_3$), 1.13–1.68 (24H, m, ester CH$_3$+alkylene chain), 2.42 (2H, t, J 6.3 Hz, ≡—CH$_2$), 4.23 (2H, q, J 7.5 Hz, ester CH$_2$), 4.26 (2H, q, J 7.5 Hz, ester CH$_2$), 7.31 (4H, m, aromatics), 8.20 (1H, s, CHO), M+ 426.2780 ($C_{27}H_{38}O_4$ requires; 426.2770).

EXAMPLE 7

Diethyl 2-[2-(1-tridecynyl)phenyl]methylenepropan-1,3-dioate

A solution of 2-(1-tridecynyl)benzaldehyde (6.42, 22.6 mmol from example 3) was condensed with diethyl malonate (3.72 g) as described in example 1 to give 2.00 g (21%, 36% on the basis of unrecovered starting material) of the title compound identical with that prepared in example 6 above.

EXAMPLE 8

Diethyl 2-[4-(1-tridecynyl)phenyl]methylenepropan-1,3-dioate

The method followed was that described in example 3 to give the title compound in 35% yield, as an oil after chromatography.

Found: C, 76.10; H, 9.20; $C_{27}H_{38}O_4$ required: C, 76.02, H, 8.98%.

EXAMPLE 9

Diethyl 2-[4-(1-octynyl)phenyl]methylenepropan-1,3-dioate

The method described in example 3 was followed to give the title compound as an oil in 32% yield after chromatography.

$M^+$ 356.1990 ($C_{22}H_{28}O_4$ requires 356.1988)

EXAMPLE 10

Diethyl 2-(2-[(Z)-1-tridecenyl]phenyl)methylenepropan-1,3-dioate

5% Palladium on barium sulphate (64 mg) was added to a solution of diethyl 2-[2-(1-tridecynyl)phenyl]methylenepropan-1,3-dioate (1.28 g, 3 mmol, from example 6) in pyridine (20 ml) and the mixture was hydrogenated at atmospheric pressure until 1 equivalent of hydrogen was absorbed. The catalyst was removed by filtration and the pyridine evaporated in vacuo to leave an oil. Chromatography on 10% argentated silica gel eluting with dichloromethane:petroleum ether [bp 60°–80° C.] (3:2) gave 0.91 g (71%) of the Z-alkene as a pale yellow oil, $v_{max}$ 1065, 1205, 1250, 1630, 1730, 2850, 2920 cm$^{-1}$; $\delta$(CDCl$_3$) 0.84 (3H, distorted t, terminal CH$_3$), 2.22 (24H, m, alkylene chain+ester CH$_3$), 2.00 (2H, m. allylic CH$_2$), 4.16 (2H, q, J ca 7.5 Hz, ester CH$_2$), 4.23 (2H, q, J ca 7.5 Hz, ester CH$_2$) 5.77 (1H, d.t, $J_d$ 11.5 Hz, $J_t$ 7.5 Hz, C=CH-alkyl) 6.41 (1H, d, J 11.5 Hz, ArCH=C-alkyl), 7.22 (4H, m, aromatics), 7.87 (1H, s, ArCH=C(CO$_2$R)$_2$). $M^+$428.2924 ($C_{27}H_{40}O_4$ requires, 428.2926).

EXAMPLE 11

Diethyl 2-(4-[(Z)-1-tridecenyl]phenyl)methylenepropan-1,3-dioate

The method described in example 10 was followed to give the title compound as an oil in 64% yield after chromatography.

Found: C, 75.82; H, 9.64; $C_{27}H_{40}O_4$ requires: C, 75.66; H, 9.41%.

EXAMPLE 12

Diethyl 2-(2-bromobenzyl)propan-1,3-dioate

Diethyl malonate (77 g, 0.48 mol) was added to a stirred solution of sodium (10.2 g, 0.425 mol) in ethanol (800 ml) followed by 2-bromobenzyl bromide (100 g, 0.40 mol). Sodium bromide began to separate towards the end of the addition and the mixture became warm. The reaction was completed by refluxing on a steam bath for 3 hours and then cooling overnight. The bulk of the solvent was removed in vacuo, water was added and the product extracted into ether. After drying (CaCl$_2$) and evaporation the product was distilled to give 93.28 g (71%) of material of bp$_{0.2}$ 130° C. (lit bp$_{0.004}$ 115°–120° C., F. G. Holliman and F. G. Mann *J. Chem. Soc.* 9, [1960]).

EXAMPLE 13

Diethyl 2-(4-bromobenzyl)propan-1,3-dioate

The method described in example 12 was followed to give the title compound in 50% yield as an oil (b$_{0.5}$ 133°–136° C.).

Found; C, 51.21, H, 5.26, $C_{14}H_{19}O_4$ requires; C, 51.08; H, 5.21%.

EXAMPLE 14

Diethyl 2-[2-(1-tridecynyl)phenyl]methylpropan-1,3-dioate

Reaction of diethyl(2-bromobenzyl)propan-1,3-dioate (11.87 g, 30 mmol) with 1-tridecyne (11.10 g, 45 mmol) as described in example 3 gave 3.89 g (29%) of the title compound as a pale yellow oil after chromatography. It had $v_{max}$ (film) 1735, 1755, 2840, 2920 cm$^{-1}$; $\delta$(CDCl$_3$) 0.87 (3H, distorted t, terminal CH$_3$), 1.08 (6H, t, J 7 Hz, ester CH$_3$), 1.28 (18H, m, alkylene chain), 2.42 (2H, t, J 6 Hz, C≡C—CH$_2$), 3.31 (2H, d, J 7.5 Hz, ArCH$_2$), 3.90 (1H, t, J 7.5 Hz, methine H), 4.12 (4H, q, J 7.5 Hz, ester CH$_2$), 7.15 (3H, m, aromatics), 7.36 (1H, m, aromatic). $M^+$ 428.2928 ($C_{27}H_{40}O_4$ requires; 428.2926).

EXAMPLE 15

4-[(Z)1-Undecenyl]phenol

Sodium hydride, (1.68 g, 0.035 mol of a 50% dispersion in mineral oil) was washed by decantation with petroleum ether bp 60°–80° C. and added to dry deaerated dimethylsulphoxide (40 ml) under nitrogen. The mixture was stirred at 75° C. for 0.5 h, cooled to 5° C. in an ice bath and a solution of n-decyltriphenylphosphonium bromide (16.78 g, 0.035M) in dimethylsulphoxide, (50 ml), added. The red solution was stirred for 15 min. and then treated dropwise with 4-hydroxybenzaldehyde, sodium salt, (5.10 g, 0.035M) in dry deaerated dimethylsulphoxide, (30 ml) at 10° C. After stirring at room temperature for 3 h, the mixture was poured into water, acidified with dilute hydrochloric acid, extracted into ethyl acetate and dried, (MgSO$_4$). Evaporation of the solvent gave a red oil which was purified by column chromatography on silica gel, eluting with dichloromethane to yield 6.15 g (70%) of E/Z isomers as a white, crystalline solid. Recrystallization from petroleum ether bp 60°–80° C. gave 4.25 g (50%) of the pure Z-isomer. A second crop was also obtained as a 65:35 mixture of Z and E isomers respectively, (1.0 g, 12% yield).

Data 4-[(Z)1-undecenyl]phenol

Mp (petroleum ether, bp 60°–80° C.) 57° C. $v_{max}$ (mull) 1515, 1595, 1610, 1900 (weak) 3325 cm$^{-1}$ $\delta$(CDCl$_3$) 0.84 (3H, distorted t, terminal CH$_3$), 1.24 (14H, m, (CH$_2$)$_7$), 2.23 (2H, bt, J 6 Hz, allylic CH$_2$), 4.67 (1H, s, OH), 5.53 (1H, d.t, $J_d$ 12 Hz, $J_t$ 7 Hz, C=CH—alkyl) 6.30 (1H, d, J 12 Hz, ArCH=C), 6.96 (4H, ABq, $\Delta v$ 36 Hz, J 9 Hz, $C_6H_4$).

Found, C, 82.63, H, 10.54, $C_{17}H_{26}O$ requires, C, 82.87, H, 10.64%.

EXAMPLE 16 AND 17

2-[(Z)1-Tridecenyl]phenol. (Example 16) and 2,[(E)-1-Tridecenyl]phenol (Example 17)

Prepared according to the method described in Example 15 from salicyladehyde and dodecyltriphenylphosphonium bromide. Chromatography of the crude reaction mixture on silica gel (dichloromethane) gave 4.48 g of mixed E and Z isomers (44%). Rechromatography on silica gel (dichloromethane-hexane, 1:4) gave first 1.84 g pure Z-isomer as a colourless oil, (18%), $\nu_{max}$ (film) 3400, 1605, 1595, 1480 cm$^{-1}$, $\delta$(CDCl$_3$) 0.85 (3H, distorted t, terminal CH$_3$) 1.25 (18H, m, (CH$_2$)$_9$), 2.12 (2H, m, allylic CH$_2$), 5.00 (1H, bs, OH), 5.83 (1H, d.t, J$_d$ 12 Hz, J$_t$ 7 Hz C=CH—alkyl), 6.32 (1H, d, J 12 Hz ArCH=C), 7.00 (4H, m, aromatic).

Found; C, 81.86, H, 10.77, C$_{19}$H$_{30}$O, 0.25H$_2$O requires; C, 81.80, H, 11.02.

M.S. Observed mass 274.2298, Theoretical mass 274.2297.

Further evaluation gave the (E)-isomer (1.97 g) as a colourless oil (19%), $\nu_{max}$ (film) 3350, 1605, 1590, 1480 cm$^{-1}$, $\delta$(CDCl$_3$) 0.90 (3H, distorted t, terminal CH$_3$) 1.28 (18H, m, (CH$_2$)$_9$), 2.14 (2H, m, allylic CH$_2$), 5.15 (1H, bs, OH), 6.10 (1H, d.t, J$_d$ 16 Hz 8 HzC=CH alkyl), 6.48 (1H, d, J 16 Hz), 7.05 (4H, m, aromatic).

M.S. Observed mass 274.2304, Theoretical mass 274.2297.

EXAMPLE 18

1-Bromo-2-(4-[(Z)1-Undecenyl]phenoxy)ethane

4-[(Z)-1-Undecenyl]phenol, (2.30 g, 9.30 mmol) and anhydrous potassium carbonate, (1.93 g, 14.0 mmol) in methyl isobutyl ketone (100 ml) were stirred and treated with 1,2-dibromoethane, (5.27 g, 29 mmol). The mixture was refluxed for 24 h after which time a further aliquot of 1,2-dibromoethane, (5.27 g, 28 mmol) was added. The mixture was refluxed a further 24 h, then cooled and washed with water, (twice). The organic phase was dried, (MgSO$_4$), and evaporated in vacuo to an oil. Purification by column chromatography on silica gel, eluting with n-hexane then dichloromethane gave 1.34 g (41%) of the title compound as a white crystalline solid mp 40°-1° C. $\nu_{max}$ (mull) 1510, 1573 (weak) 1610 cm$^{-1}$, $\delta$ (CDCl$_3$) 0.86 (3H, distorted t, terminal CH$_3$), 1.26 (14H, m, (CH$_2$)$_7$), 2.26 (2H, m, allylic CH$_2$), 3.60 (2H, t, J 6 Hz, CH$_2$Br), 4.26 (2H, t, J 6 Hz, OCH$_2$) 5.56 (1H, d.t, Jd 12 Hz, Jt 7 Hz, =CH—alkyl), 6.32 (1H, d, J 12 Hz, ArCH=), 7.06 (4H, ABq, $\Delta\nu$ 33 Hz, J 9 Hz, C$_6$H$_4$).

Found, C, 64.55, H, 8.43, Br, 22.33, C$_{19}$H$_{29}$BrO requires, C, 64.58, H, 8.27, Br, 22.62%.

Mass Spec. Observed mass 352.1403, theoretical mass 352.1402 for C$_{19}$H$_{29}$BrO.

EXAMPLE 19

1-Bromo-2-(2-[(Z)1-tridecenyl]phenoxy)ethane

Prepared from 2-[(Z)-1-tridecenyl]phenol 1.70 g (Example 16) by the method described in Example 18.

After chromatography of the crude reaction mixture the title compound was isolated (1.23 g=52%). Some unreacted phenol (0.42 g) was also isolated. (Yield based on phenol consumed 69%) $\nu_{max}$ 1600, 1450, 1240, 745 cm$^{-1}$, $\delta$(CDCl$_3$) 0.92 (3H, distorted t, terminal CH$_3$), 1.28 (18H, m, (CH$_2$)$_9$) 2.22 (2H, m, allylic CH$_2$), 3.57 (2H, t, CH$_2$Br), 4.22 (2H, t, OCH$_2$), 5.65 (1H, d.t, J$_d$ 12 Hz, J$_t$ 7 Hz, C=CH alkyl), 6.58 (1H, d, ArCH=C), 7.05 (4H, m, aromatic).

Found; C, 66.22, H, 8.80, Br, 20.66%, C$_{21}$H$_{33}$BrO requires, C, 66.12, H, 8.72, Br, 20.95%.

M.S. Observed mass 380.1719, Theoretical mass 380.1715.

EXAMPLE 20

1-Bromo-2-(2-[(E)-1-tridecenyl]phenoxy)ethane

Prepared from 2-[(E)-1-tridecenyl]phenol 1.05 g (Example 17) by the method described in Example 18).

Chromatography on silica gel (Dichloromethane-hexane 1:4) gave the product (0.93 g=64%) as a pale yellow oil, $\nu_{max}$ 1600, 1490, 1455, 1240, 745 cm$^{-1}$, $\delta$(CDCl$_3$) 0.95 (3H, distorted t, terminal CH$_3$), 1.30 (18H, m, (CH$_2$)$_9$), 2.22 (2H, m, allylic CH$_2$), 3.63 (3H, t, CH$_2$Br), 4.25 (3H, t, OCH$_2$), 6.22 (1H, d.t, J$_d$ 16 Hz, J$_t$ 8 Hz, C=CH alkyl) 6.62, (1H, d, J 16 Hz, ArCH=C), 7.10 (4H, m, aromatic).

Found; C, 65.95, H, 8.77, Br 21.11%, C$_{21}$H$_{33}$BrO requires; C, 66.12, H, 8.72, Br 20.95%.

M.S. Observed mass 380.1705, Theoretical mass 380.1715.

EXAMPLE 21

Diethyl 2-(4-[(Z)-1-undecenyl]phenoxyethyl)propan-1,3-dioate

A solution of sodium (0.408 g, 17.7 mmol) in ethanol (50 ml) under nitrogen was treated with diethyl malonate, (2.84 g, 17.7 mmol) followed by 1-bromo-2-(4-[(Z)1-undecenyl]phenoxy)ethane, (1.30 g, 3.68 mmol). The solution was refluxed 30 h, then cooled and evaporated in vacuo to dryness. The residue was partitioned between ethyl acetate and water and the organic phase separated, washed with water, and dried, (MgSO$_4$). Evaporation in vacuo gave 2.0 g of a yellow oil which was purified by column chromatography using silica gel, eluting with dichloromethane: n-hexane, [2:3] to yield 510 mg (32%) of the title compound as a colourless oil. $\nu_{max}$ (film) 1510, 1570 (weak) 1608, 1735, 1753 cm$^{-1}$ $\delta$(CDCl$_3$) 0.84 (3H, distorted t, terminal CH$_3$), 1.25 (3H, t, J 7 Hz ester CH$_3$), 1.25 (14H, m, (CH$_2$)$_7$), 2.31 (4H, m, OCH$_2$CH$_2$, allylic CH$_2$), 3.63 (1H, t, J 7 Hz, CH(CO$_2$Et)$_2$), 4.01 (2H, t, J 7 Hz, OCH$_2$), 4.18 (4H, q, J 7 Hz, ester CH$_2$), 5.54 (1H, d.t, J$_d$ 12 Hz, J$_t$ 7 Hz, =CH—alkyl), 6.31 (1H, d, J 12 Hz, ArCH=), 7.02 (4H, ABq, $\Delta\nu$ 34 Hz, J 9 Hz, C$_6$H$_4$).

Mass Spec. Observed mass 432.2887, theoretical mass 432.2876 for C$_{26}$H$_{40}$O$_5$.

Found: C, 72.15, H, 9.49, C$_{26}$H$_{40}$O$_5$ requires; C, 72.19, H, 9.32%.

EXAMPLE 22

Diethyl 2-(2-[(z)-1-tridecenyl]phenoxyethyl)propan-1,3-dioate

Prepared from the bromoethyl compound (1.20 g) (Example 19) and diethylmalonate by the method described in Example 21. Chromatography of the crude product on silica gel (dichloromethane-hexane 3:7) gave the product 0.81 g (60%) as a colourless oil. $\nu_{max}$ 1750, 1730, 1600, 1450, 1240, 745 cm$^{-1}$, $\delta$(CDCl$_3$) 0.90 (3H, distorted t, terminal CH$_3$), 1.28 (24H, m, (CH$_2$)$_9$+2 x ester CH$_3$), 2.35 (4H, m, allylic CH$_2$+CH$_2$CH(CO$_2$Et)$_2$), 3.70 (1H, t, CH$_2$CH (CO$_2$Et)$_2$), 4.22 (6H, m, OCH$_2$+2 x ester CH$_2$), 5.65 (1H, d.t, $J_d$ 12 Hz, $J_t$ 7 Hz, C≡CH alkyl), 6.48 (1H, d, J 12 Hz ArCH=C), 7.00 (4H, m, aromatic).

Found, C, 72.75, H, 9.46%, $C_{28}H_{44}O_5$ requires C, 73.00, H, 9.63%.

M.S. Observed mass 460.3188, theoretical mass 460.3189.

EXAMPLE 23

Diethyl 2-(2-[(E)-1-tridecenyl]phenoxyethyl)propan-1,3-dioate

Prepared from the bromoethyl compound (0.70 g) (Example 20) and diethylmalonate by the method described in Example 21. Chromatography of the crude product on silica gel (dichloromethane-hexane 1:4) gave the product 0.42 g (50%) as a colourless oil, $\nu_{max}$ 1755, 1735, 1600, 1240, 745 cm$^{-1}$, δ(CDCl$_3$) 0.92 (3H, distorted t, terminal CH$_3$), 1.30 (24H, m, (CH$_2$)$_9$)+2 x ester CH$_3$), 2.23 (2H, m, allylic CH$_2$), 2.42 (2H, q, CH$_2$CH(CO$_2$Et$_2$)), 3.65 (1H, t, CH$_2$CH(CO$_2$Et)$_2$), 4.15, (6H, m, OCH$_2$+2 x ester CH$_2$), 6.17 (1H, d.t, $J_d$ 16 Hz, $J_t$ 8 Hz C=CH alkyl), 6.58 (1H, d, J 16 Hz, ArCH=C), 7.00 (4H, m, aromatic).

Found, C, 73.05, H, 9.73%, $C_{28}H_{44}O_5$ requires, C, 73.00, H, 9.63%.

M.S. Observed mass 460.3197, Theoretical mass 460.3189.

EXAMPLES 24–33 (Tables I and II)

General hydrolysis procedures (a) Mono acids—A solution of the diester (10 mmol) in tetrahydrofuran (20 ml) was added to a solution of lithium hydroxide monohydrate (420 mg, 10 mmol) in water (10 ml) and the mixture was stirred at 30→60° C. until neutral (≦24 hrs). The mixture was then cooled and acidified with dilute hydrochloric acid and the product extracted into ether. The ethereal phase was dried (MgSO$_4$) and evaporated and the residue either recrystallized or chromatographed on silica gel to give pure mono acids. Small samples of the diacids were sometimes isolated by this procedure also.

(b) Diacids—A mixture of the diester (3 mmol) in water (20 ml) containing potassium hydroxide (1.8 g) was stirred at 100° C. for 6→24 hrs and the resulting clear solution was cooled, added to an equal volume of water and evaporated to one half its bulk in vacuo. Acidification then yielded the product which was either filtered off and recrystallized or isolated by ethereal extraction.

TABLE I

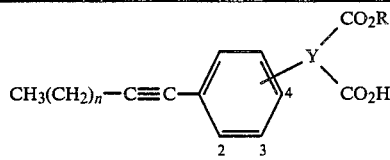

| Example No. | n | Y | Position of Y attachment | R | Yield % | mp, °C. | Recrystallization Solvent | Formula | Analysis (calcd/found) C | H |
|---|---|---|---|---|---|---|---|---|---|---|
| 24 | 10 | CH=C | 2 | Et | 66 | 48–50 | petroleum ether bp 60–80° C. | $C_{25}H_{34}O_4$ | 75.34 / 75.36 | 8.60 / 8.69 |
| 25 | 10 | CH=C | 2 | H | 79 | 93–96 | petroleum ether bp 80–100° C. | $C_{23}H_{30}O_4.0.5H_2O$ | 72.79 / 72.78 | 8.23 / 8.31 |
| 26 | 10 | CH=C | 4 | Et | 64 | 94–95 | hexane | $C_{25}H_{34}O_4$ | 75.34 / 75.17 | 8.59 / 8.49 |
| 27 | 10 | CH=C | 4 | H | 59 | 99–100 | hexane | $C_{23}H_{30}O_4$ | 75.34 / 75.16 | 8.60 / 8.71 |
| 28 | 10 | CH$_2$CH$_2$ | 2 | H | 68 | 85–86 | petroleum ether bp 60–80° C. | $C_{23}H_{32}O_4$ | 74.16 / 74.14 | 8.66 / 8.57 |

TABLE II

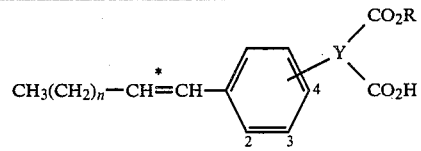

| Example No. | n | Y | Position of Y attachment | R | Geometry of *double bond | Yield % | mp, °C. | Recrystallization solvent | Formula | Analysis (calcd/found) C | H |
|---|---|---|---|---|---|---|---|---|---|---|---|
| 29 | 10 | CH=C | 2 | H | Z | 57 | 83–84 | petroleum ether bp 80–100° C. | $C_{23}H_{32}O_4$ | 74.16 / 74.06 | 8.67 / 8.34 |
| 30 | 10 | CH=C | 4 | Et | Z | 51 | 86–90 | hexane | $C_{25}H_{36}O_4$ | 74.96 / 74.91 | 9.06 / 9.18 |
| 31 | 8 | O(CH$_2$)$_2$CH | 4 | Et | Z | 46 | Oil | — | $C_{24}H_{36}O_5$ | 71.26 / 71.00 | 8.97 / 9.12 |
| 32 | 10 | O(CH$_2$)$_2$CH | 2 | Et | Z | 69 | Oil | — | $C_{26}H_{40}O_5$ O:25H$_2$O | 71.44 / 71.45 | 9.34 / 9.31 |
| 33 | 10 | O(CH$_2$)$_2$CH | 2 | Et | E | 22 | Oil | — | $C_{26}H_{40}O_5$ | M$^+$ 432.2882 (calcd. M$^+$ 432.2876.) | |

EXAMPLE 34

3-(Tridec-1-ynyl)benzyl alcohol

To a solution of 3-(Tridec-1-ynyl)benzaldehyde (5.68 g, 20 mmol, from example 5) in THF (70 ml) at −78° C. was added DIBAL (22 ml, 1.1 eq, 1 molar solution in hexane). After warming slowly to room temperature the solution was stirred for 2 hr and then added to dilute hydrochloric acid (50 ml). The product was then extracted into diethyl ether (2×100 ml) and after washing with brine and drying (MgSO$_4$) the ether was removed under reduced pressure. Distillation of the resulting oil yielded the desired product, (4.55 g, 79.5%), B.p. 210° C. at 0.1 mm Hg, $\nu$max 690, 785, 1030, 1460, 1600, 2200, 2850, 2915 and 3300 cm$^{-1}$; $\delta$(CDCl$_3$) 0.92 (3H, distorted t, terminal CH$_3$), 1.3 (18H, m, alkylene chain), 1.9 (1H, s, hydroxyl), 2.35 (2H, t J=7 Hz, CH$_2$ adjacent to acetylene), 4.6 (2H, s, benzylics), 7.3 (4H, m, aromatics). M$^+$ 286.2301, (C$_{20}$H$_{30}$O requires 286.2297).

Found: C, 83.30; H, 10.53; C$_{20}$H$_{30}$O.$\frac{1}{4}$H$_2$O requires: C, 83.30; H, 10.57.

EXAMPLE 35

3-(Tridec-1-ynyl)benzyl bromide

Triphenyl phosphine (1.5 g, 5.7 mmole) was added in small portions to a stirred solution of 3-(Tridec-1-ynyl)-benzyl alcohol (1.34 g, 4.7 mmol, from example 34) and carbon tetrabromide (1.87 g, 5.7 mmole) in dichloromethane (20 ml) at 0° C., and the mixture was stirred for a further 3 hr at this temperature. After removing all the solvent under reduced pressure, n-hexane (20 ml) was added and the precipitate of triphenylphosphine oxide removed by filtration. Removal of the hexane under reduced pressure gave an oil which was distilled to give the desired product, (1.49 g, 91%) B.p. 170° C. at 0.05 mmHg., $\nu$max 690, 790, 1210, 1460, 1480, 1600, 2220, 2850, 2920 cm$^{-1}$, $\delta$(CDCl$_3$) 0.7 (3H, distorted t, terminal CH$_3$), 1.2 (18H, m, alkylene chain), 2.16 (2H, t J=7 Hz, CH$_2$ adjacent to acetylene), 4.15 (CH, s, benzylics), 7.06 (4H, m, aromatics).

EXAMPLE 36

4-(1-Octynyl)benzyl alcohol

To a solution of 4-(1-octynyl)benzaldehyde (15 g, 0.07 mole from example 4) in ethanol (200 ml) was added sodium borohydride (1.32 g, 0.035 mole) in ethanol and the mixture was stirred for 5 minutes until no further aldehyde remained. The solution was concentrated, ether was added and the solution was washed with water and dried (MgSO$_4$). Evaporation gave an oil which was chromatographed on silica eluting with dichloromethane to give 12.5 g (82%) of the alcohol as an oil, $\nu$max (film) 815, 840, 1020, 1040, 1510, 2220, 3300 cm$^{-1}$; $\delta$(CDCl$_3$) 0.88 (3H, distorted t, terminal CH$_3$), 1.1–1.8 (8H, m, alkylene chain), 2.2 (1H exchangeable, OH), 2.36 (2H, t, J 7 Hz, CH$_2$—C≡C), 4.56 (2H, s, CH$_2$O), 7.3 (4H, ABq, aromatics). M$^+$ 216.1524 (C$_{15}$H$_{20}$O requires, 216.1514).

EXAMPLE 37

4-(1-Octynyl)benzyl bromide

Triphenyl phosphine (1.44 g, 5.5 mmole) was added in small portions to a stirred solution of 4-(1-octynyl)-benzyl alcohol (1.0 g, 4.6 mmole, from example 36) and carbon tetrabromide (1.82 g, 5.5 mmole) in dichloromethane (20 ml) at 0° C., and the mixture was stirred for a further 3 hours at this temperature. Flash chromatography of the concentrated material on silica eluting with dichloromethane:hexane (1:5) and then dichloromethane gave 1.3 g (100%) of the bromide as an oil, $\nu$max (film) 670, 835, 1200, 1220, 1510, 1610, 2220 cm$^{-1}$; $\delta$(CDCl$_3$) 0.8 (3H, distorted t, terminal CH$_3$), 1.7–1.9 (8H, m, alkylene chain), 2.35 (2H, t, J 6 Hz, CH$_2$C≡C), 4.4 (2H, s, CH$_2$Br.), 7.3 (4H, s, aromatics). M$^+$ 278.0678 (C$_{15}$H$_{19}$Br requires, 278.0670).

Found: C, 64.72; H, 7.05; C$_{15}$H$_{19}$Br requires: C, 64.52; H, 6.85.

EXAMPLE 38

1-(3-Methoxyphenyl)-oct-1-yne

3-Methoxyphenylacetylene [5.00 g, 0.032M, prepared by the method of E. Negishi et al, J. Org. Chem. 45 2526–8, (1980)] was dissolved in dry tetrahydrofuran (15 ml), cooled to −70° C. under nitrogen, and n-butyl lithium, 1.6M in hexane, (24.40 ml, 0.038M), added dropwise. After stirring for 0.5 h, iodohexane (8.00 g, 0.038M), dissolved in dry tetrahydrofuran, (15 ml) was added dropwise. The rection was warmed slowly to room temperature, refluxed overnight, then cooled. The solution was then quenched with water, acidified with dilute hydrochloric acid and extracted with diethyl ether (twice). The organic phases were combined, washed with water and dried, (MgSO$_4$). Evaporation in vacuo affored 7.71 g of product as an orange oil.

Purification by distillation gave 6.98 g (85%) of the product as a colourless oil, bp 150°–60° C., (Kugelröhr). $\nu$max (film) 1465, 1480, 1490 (wk), 1575, 1585, 1600, 1605, 2225, (wk) cm$^{-1}$; $\delta$(CDCl$_3$) 0.88 (3H, distorted t, terminal CH$_3$), 1.37 (8H, m, alkylene chain), 2.36 (2H, t, J 6 Hz, acetylenic CH$_2$), 3.74 (3H, s, OCH$_3$), 6.92 (3H, m, aromatics), 7.16 (1H, t, J 7 Hz, aromatic).

Found: C, 82.05; H, 9.39; C$_{14}$H$_{20}$O.0.25H$_2$O requires: C, 81.59; H, 9.36%.

M$^+$216.1504 (C$_{15}$H$_{20}$O requires 216.1514).

EXAMPLE 39

1-(3-Hydroxyphenyl)-oct-1-yne 1-(3-Methoxyphenyl)-oct-1-yne, (6.50 g, 0.03M), was dissolved in 2,4,6-collidine, (100 ml), and anhydrous lithium iodide (20.08 g, 0.15M), added. The reaction was stirred under nitrogen at reflux temperature for 48 h, then cooled and poured intro water, (500 ml), and acidified with dilute hydrochloric acid. The product was extracted into ethyl acetate, (twice), and the organic phases combined, washed with water (twice) and dried, (MgSO$_4$). Evaporation of the solvent in vacuo yielded the crude product as a brown oil, which was purified by chromatography on silica gel, eluting with dichloromethane/n-hexane [1:1] to chloroform. 5.40 g (90%) of product was collected as a colourless oil. $\nu$max (film) 1580, 1590, 1605, 2230 (weak) 3400 cm$^{-1}$; $\delta$(CDCl$_3$) 0.85 (3H, distorted t, terminal CH$_3$), 1.39 (8H, m, alkylene chain), 2.32 (2H, t, J 6 Hz, acetylenic CH$_2$), 4.77 (1H, s, OH, exchanged with D$_2$O), 6.78 (2H, m, aromatics), 7.02 (2H, m, aromatics).

Found: C, 84.14; H, 9.01; C$_{14}$H$_{18}$O requires: C, 83.12; H, 8.97%.

M$^+$202.1357 (C$_{14}$H$_{18}$O requires 202.1357).

EXAMPLE 40

Diethyl 2-{3-[3-(1-Octynyl)phenoxy]propyl}propan-1,3-dioate 1-(3-Hydroxyphenyl)-oct-1-yne, (2.20 g, 0.01M) and diethyl 2-(3-hydroxypropyl)propane-1,3-dioate [2.40 g, 0.01M, (prepared by the method of A.G. Just et al, Tet. Letts., 3645-3647, (1979)] were dissolved in dry tetrahydrofuran, (50 ml) and triphenylphosphine, (4.20 g, 0.016M), added. The solution was stirred at 10° C. and diethyl azodicarboxylate, (2.80 g, 0.016M), added dropwise. The reaction was stirred for 0.5 h after which time TLC showed some unreacted phenol remaining. Further aliquots of the alcohol, (2.40 g, 0.01M), triphenylphosphine, (4.20 g, 0.016M) and dietyl azodicarboxylate (2.80 g, 0.016M) were added and the reaction stirred for 0.5 h. Evaporation of the solvent in vacuo gave a red oil which was purified by chromatography on silica gel eluting with dichloromethane→chloroform, to yield 0.770 g (19%) of the title compound as a colourless oil. $\nu$max (film 1580, 1600, 1610, 1740, 1758, 2225 (weak) cm$^{-1}$; $\delta$(CDCl$_3$) 0.87 (3H, distorted t, terminal CH$_3$), 1.26 (6H, t, J 7 Hz, 2×ester CH$_3$), 1.33 (8H, m, alkylene chain), 1.93 (4H, m, OCH$_2$CH$_2$CH$_2$), 2.34 (2H, t, J 6 Hz, acetylenic CH$_2$), 3.37 (1H, t, J 7 Hz, CH), 3.91 (2H, t, J 6 Hz, OCH$_2$), 4.16 (4H, q, J 7 Hz, 2×ester CH$_2$), 7.00 (4H, m, aromatics).

Found: C, 70.51; H, 8.46; C$_{24}$H$_{34}$O$_5$.0$_{25}$H$_2$O requires: C, 70.82; H, 8.54%.

M$^+$ 402.2416 (C$_{24}$H$_{34}$O$_5$ requires 402.2406).

EXAMPLE 41

1-(2-Hydroxyphenyl)-oct-1-yne

To a grey suspension of lithium amide [lithium shot, (0.59 g, 0.085M) in liquid ammonia (250 ml)] at −30° C. was added 2-hydroxyphenyl acetylene (50 g, 0.042M, prepared by the method of G. A. Russell et al, J. Org. Chem. 31, 248 (1966)) in dry tetrahydrofuran (50 ml). The solution was stirred at reflux for 1 h, then iodohexane (8.91 g, 0.042M), in dry tetrahydrofuran (50 ml) was added dropwise. The reaction was refluxed for 6 h, then the ammonia allowed to evaporate overnight. The resultant pale brown solution was refluxed for 18 h, then cooled and poured into water. Acidified with dilute sulphuric acid and extracted into diethyl ether (twice). The combined organic phases were washed with water (twice), saturated brine and dried (MgSO$_4$). Evaporation in vacuo yielded a red oil which was purified by distillation to give 6.80 g (80%) of the product as a colourless oil. $\nu$max (film) 1463, 1485, 1575, 1608 (weak), 2225 (weak), 3500 cm$^{-1}$, $\delta$(CDCl$_3$) 0.89 (3H, distorted t, terminal CH$_3$) 1.40 (8 H, m, alkylene chain), 2.43 (2H, t, J 7 Hz, acetylenic CH$_2$), 5.80 (1H, s, OH), 6.87 (2H, m, aromatics) 7.22 (2H, m, aromatics).

Found: C, 79.64; H, 8.78; C$_{14}$H$_{18}$O.0.5H$_2$O requires: C, 79.58; H, 9.06%.

M$^+$ 202.1363 (C$_{14}$H$_{18}$O requires 202.1358).

EXAMPLE 42

(Z) 3-(1-Octenyl)-phenol

Sodium hydride, (3.10 g, 0.077M of a 60% dispersion in oil) was washed by decantation with petroleum ether, bp 60°-80° C. and added to dry, deaerated dimethylsulphoxide, (160 ml), under nitrogen. The mixture was stirred at 75° C. for 0.75 h then cooled to 5° C. A solution of n-heptyltriphenylphosphonium bromide, (34.0 g, 0.077M) in dimethylsulphoxide, (40 ml) was added and the red solution stirred for 15 min. 3-Hydroxybenzaldehyde, sodium salt [9.40 g, 0.077M of 3-hydroxy benzaldehyde in dimethylsulphoxide, (40 ml), treated with one molar equivalent of sodium hydride] was added dropwise at 10° C. and the reaction stirred at 10° C. for 1 h and at room temperature for 3 h.

The pale brown mixture was then poured into 10% brine (600 ml), acidified with dilute hydrochloric acid and extracted into hexane, (twice). The combined organic phases were washed with water (twice), brine and then dried, (MgSO$_4$). Evaporation of the solvent and purification by column chromatography using silica gel, eluting with dichloromethane/n-hexane [1:4] yield 7.1 g (45%) of the single Z isomer as a colourless oil. $\nu$max (film) 1490, 1580, 1590, 1610, 3340 cm$^{-1}$; $\delta$(CDCl$_3$) 0.83 (distorted t, terminal CH$_3$), 1.27 (8H, m, alkylene chain), 2.23 (2H, m, allylic CH$_2$), 5.20 (1H, bs, OH, exchanged with D$_2$O), 5.60 (1H, d.t, J$_d$ 11 Hz, J$_t$ 7 Hz, =CHCH$_2$), 6.30 (1H, d, J 11 Hz ArCH=), 6.73 (2H, m, aromatics), 7.16 (1H, m, aromatic), 7.56 (1H, m, aromatic).

Found: C, 80.59; H, 9.57; C$_{14}$H$_{20}$O.0.25H$_2$O requires: C, 80.53; H, 9.90%.

TABLE 3

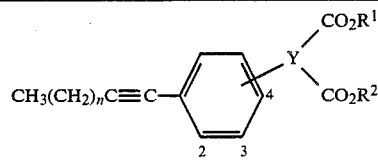

| Example No. | n | Y | Position of Y attachment | R$^1$ | R$^2$ | Yield % | mp, °C. | Recrystallization Solvent | Prepared by method of example no. | Formula | Analysis (calcd/found) C | H |
|---|---|---|---|---|---|---|---|---|---|---|---|---|
| 43 | 10 | CH=C | 3 | Et | Et | 76 | oil | — | 1 | C$_{27}$H$_{38}$O$_4$ | M$^+$ 426.2780 calcd. 426.2770 | |
| 44 | 5 | CH=C | 4 | Et | Et | 32 | oil | — | 3 | C$_{22}$H$_{28}$O$_4$ | M$^+$ 356.1990 calcd. 356.1988 | |
| 45 | 5 | CH=C | 4 | Me | Me | 54 | oil | — | 1 | C$_{20}$H$_{24}$O$_4$ | 73.14 73.46 | 7.37 7.51 |
| 46 | 10 | CH$_2$CH | 3 | Et | Et | 45 | oil | — | 12 | C$_{27}$H$_{40}$O$_4$ | 75.66 75.76 | 9.41 9.44 |
| 47 | 5 | CH$_2$ | 4 | Et | Et | 73 | oil | — | 12 | C$_{22}$H$_{30}$O$_4$ | 73.71 73.92 | 8.43 8.32 |
| 48 | 5 | CH=C | 4 | Et | H | 98 | 85-88 | Hexane | 24 | C$_{20}$H$_{24}$O$_4$ | 73.14 73.11 | 7.37 7.44 |
| 49 | 5 | CH=C | 4 | Me | H | 71 | 106-110 | Hexane | 24 | C$_{19}$H$_{22}$O$_4$ | 72.59 | 7.05 |

TABLE 3-continued

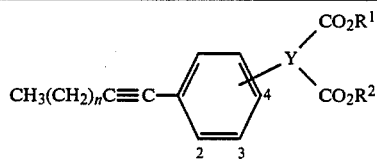

| Example No. | n | Y | Position of Y attachment | $R^1$ | $R^2$ | Yield % | mp, °C. | Recrystallization Solvent | Prepared by method of example no. | Formula | Analysis (calcd/found) C | H |
|---|---|---|---|---|---|---|---|---|---|---|---|---|
| 50 | 5 | CH≡C | 4 | H | H | 63 | 137–138 | Petroleum ether [bp 80-100° C.] | 24 | $C_{18}H_{20}O_4$ | 72.33 71.98 71.65 | 7.20 6.71 6.72 |
| 51 | 10 | CH≡C | 3 | H | H | 76 | 106–107 | Petroleum ether 80-100° C. | 24 | $C_{23}H_{30}O_4$ | 74.56 74.36 | 8.16 8.35 |
| 52 | 10 | $CH_2CH$ | 3 | H | H | 95 | 81–82 | Petroleum ether 80-100° C. | 24 | $C_{23}H_{32}O_4$ | 74.16 73.93 | 8.66 8.82 |
| 53 | 5 | $CH_2CH$ | 4 | H | H | 83 | 115–6 | Petroleum ether 80-100° C. | 24 | $C_{18}H_{22}O_4$ | 71.50 71.55 | 7.33 7.38 |
| 54 | 5 | $O(CH_2)_3CH$ | 2 | Et | Et | 42 | oil | — | 40 | $C_{24}H_{34}O_5$ .0.5$H_2O$ | 70.05 69.70 69.61 | 8.57 |
| 55 | 5 | $O(CH_2)_3CH$ | 2 | Et | H | 52 | oil | — | 24 | $C_{22}H_{30}O_5$ .0.5$H_2O$ | 68.93 69.01 | 8.15 8.17 |
| 56 | 5 | $O(CH_2)_3CH$ | 3 | Et | H | 64 | oil | — | 24 | $C_{22}H_{30}O_5$ .0.25$H_2O$ | 69.72 69.84 | 8.11 7.91 |
| 57 | 5 | $O(CH_2)_3CH$ | 2 | H | H | 93 | oil | — | 24 | $C_{20}H_{26}O_5$ .0.5$H_2O$ | 67.58 67.30 | 7.66 7.92 |
| 58 | 5 | $O(CH_2)_3CH$ | 3 | H | H | 90 | oil | — | 24 | $C_{20}H_{26}O_5$ | 69.34 69.64 | 7.57 7.47 |
| 73 | 5 | $CHCH_2$ | 4 | Et | H | 63 | oil | — | 24 | $C_{20}H_{26}O_4$ .0.5$H_2O$ | 70.77 70.38 | 8.02 7.80 |

TABLE 4

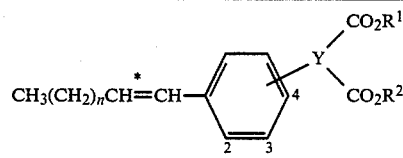

| Example No. | n | Y | Position of Y attachment | $R^1$ | $R^2$ | Geometry of *double bond | Yield % | mp, °C. | Recrystallization Solvent | Prepared by method of example no. | Formula | Analysis (calcd/found) C | H |
|---|---|---|---|---|---|---|---|---|---|---|---|---|---|
| 59 | 10 | CH=C | 3 | Et | Et | Z | 54 | oil | — | 10 | $C_{27}H_{40}O_4$ | 75.66 75.59 | 9.41 9.52 |
| 60 | 5 | CH=C | 4 | Me | Me | Z | 62 | oil | — | 10 | $C_{20}H_{26}O_4$ | 73.15 73.46 | 7.37 7.51 |
| 61 | 5 | CH=C | 4 | Et | Et | Z | 82 | oil | — | 10 | $C_{22}H_{30}O_4$ | 73.71 73.55 | 8.43 8.42 |
| 62 | 5 | CH=C | 4 | Me | H | Z | 63 | 57–60 | Hexane | 24 | $C_{19}H_{24}O_4$ | 72.12 71.84 | 7.65 7.59 |
| 63 | 10 | CH=C | 3 | H | H | Z | 93 | 78–79 | Petroleum ether bp 80-100° C. | 24 | $C_{23}H_{32}O_4$. 0.25$H_2O$ | 73.29 73.12 | 8.69 8.55 |
| 64 | 5 | CH=C | 4 | H | H | Z | 100 | 72–75 | — | 24 | $C_{18}H_{22}O_4$. 0.25$H_2O$ | 70.91 70.85 | 6.78 7.28 |
| 65 | 10 | $CH_2CH$ | 3 | Et | Et | Z | 72 | oil | — | 10 | $C_{27}H_{42}O_4$ | $M^+$ 430.3089 calcd. 430.3083 | |
| 66 | 10 | $CH_2CH$ | 3 | H | H | Z | 95 | 57–58 | Hexane | 24 | $C_{23}H_{34}O_4$ | 73.76 73.45 | 9.15 9.24 |
| 67 | 5 | $O(CH_2)_3CH$ | 3 | Et | Et | Z | 71 | oil | — | 40 | $C_{24}H_{36}O_5$ | 71.26 71.28 | 8.97 9.03 |
| 68 | 5 | $O(CH_2)_3CH$ | 3 | Et | H | Z | 99 | oil | — | 24 | $C_{22}H_{32}O_5$ | 70.18 69.98 | 8.57 8.17 |
| 69 | 5 | $O(CH_2)_3CH$ | 3 | H | H | Z | 90 | 71 | Hexane | 24 | $C_{20}H_{28}O_5$. 0.25$H_2O$ | 68.05 68.25 | 8.14 8.11 |
| 70 | 5 | $CH_2CH$ | 4 | Et | Et | Z | 85 | oil | — | 10 | $C_{22}H_{32}O_4$ | $M^+$ 360.2306 calcd. 360.2310 | |
| 71 | 5 | $CH_2CH$ | 4 | Et | H | Z | 34 | oil | — | 24 | $C_{20}H_{26}O_4$. 0.5$H_2O$ | 70.77 70.38 | 8.02 7.80 |

TABLE 4-continued $$CH_3(CH_2)_n CH{=}CH\underset{\underset{3}{\phantom{X}}}{\overset{\overset{*}{\phantom{X}}}{\left\langle\begin{array}{c}\phantom{XX}\\ \phantom{XX}\end{array}\right\rangle}}_4 Y\genfrac{}{}{0pt}{}{CO_2R^1}{CO_2R^2}$$

| Example No. | n | Y | Position of Y attachment | $R^1$ | $R^2$ | Geometry of *double bond | Yield % | mp, °C. | Recrystallization Solvent | Prepared by method of example no. | Formula | Analysis (calcd/found) C | H |
|---|---|---|---|---|---|---|---|---|---|---|---|---|---|
| 72 | 5 | CH$_2$CH | 4 | H | H | Z | 74 | 82–85 | Hexane | 24 | C$_{18}$H$_{24}$O$_4$ | 71.02 71.11 | 7.95 7.96 |

PHARMACOLOGICAL DATA

(1) RBL-1 5-Lipoxygenase Screen

5-Lipoxygenase enzyme was prepared as a 10,000 g supernatant from RBL-1 cells by the method of Jakschik (Jakschik, B. A., F. F. Sun, L. M. Lee, and M. M. Steinhoff, 1980, Biochem. Biophys. Res. Comm. 95, 103). The 10,000 g supernatant was diluted with homogenization buffer to the equivalent of $1.5$–$2.5 \times 10^7$ cells. ml.$^{-1}$ and made 2 mM with respect to CaCl$_2$. Aliquots of 0.5 ml were then dispensed into tubes, and incubated at 29° C. with 5 μl ethanol or compound in ethanol at the desired concentration for 2 min. Then [1-$^{14}$C] arachidonic acid was added in buffer to give a final concentration of 6.3 μM and 0.2 μCi per incubation, and the reaction continued at 29° C. for 2 min. The reaction was terminated by adding 1 ml of acetone and cooling on ice, 0.5 ml of ice-cold saline and 100 μl of 2M formic acid were added, and the mixture was extracted with 2×2 ml of chloroform. The extract was stored under N$_2$ at −20° C. until analysis by chromatography. Activity was measured as the percentage of total radioactivity found in 5-HETE and 5,12-diHETE, and inhibition calculated as the decrease in formation of the sum of these two species in compound-treated incubates relative to control incubations.

(2) Cyclo-oxygenase Screen

The inhibition of cyclo-oxygenase was measured in a buffered incubation (0.2M Tris-HCl, pH 8.0, containing 1 mM ethylene diaminetetraacetic acid) comprising 0.96 mg lyophilised bovine seminal vesicle microsomes, 5–15 μM arachidonic acid containing 0.2 μCi [1-$^{14}$C] arachidonic acid, 2 mM reduced glutathione, 0.5 mM hydroquinone, 1 μM haemoglobin and compound (0–0.05 mM in 5 μl dimethylsulphoxide or absolute ethanol) in a total volume of 2.0 ml. Compounds were preincubated with the incubation constitutents for 5 min at 37° C. before the reaction was started by the addition of the arachidonic acid. The reaction was continued at 37° C. for 2 min, then stopped by placing the incubations on ice and the addition of 1.2 ml 0.2M citric acid. Unmetabolised substrate and prostaglandin products were extracted in ethyl acetate (2×4 ml), the combined extracts washed with 0.8 ml water, and separated by thin-layer chromatography (Kieselgel GF$_{254}$ plates in ethyl acetate:acetone:glacial acetic acid, 90:10:1, v/v). Recovery was 65–80%. The regions on the thin-layer chromatography plate that chromatographed with authentic arachidonic acid or prostaglandins E$_2$ and F$_{2\alpha}$ (R$_f$'s 0.70, 0.28 and 0.16 respectively) were scrapped and the radioactivity in each determined by liquid scintillation counting with a correction for quenching being made by the external standard-channels ratio method. Inhibition of cyclo-oxygenase activity was calculated from the decrease in prostaglandin formation. Each compound concentration was tested in triplicate and the 50% inhibitory concentration, if determined, was calculated by linear regression from the inhibitory data at, at least three different compound concentrations.

| | BIOLOGICAL RESULTS | |
|---|---|---|
| Example No. | 5-Lipoxygenase Inhibition at 20 μM | Cyclo-Oxygenase Inhibition at 50 μM |
| 24 | 60* | 70 |
| 25 | 55* | 59 |
| 27 | | 59 |
| 28 | 63 | 76 |
| 29 | 67 | |
| 49 | 15 | |
| 50 | 16 | |
| 51 | 25 | |
| 52 | 51 | |
| 55 | 63 | |
| 56 | 52* | |
| 57 | 54 | |
| 58 | 45* | 38 |
| 63 | 82 | |
| 64 | 49 | |
| 66 | 84 | |
| 68 | 62.5 | 40 |
| 69 | 44 | |
| 71 | 30 | |

*Indicates inhibition at 50 μM

I claim:
1. A compound of formula (I):

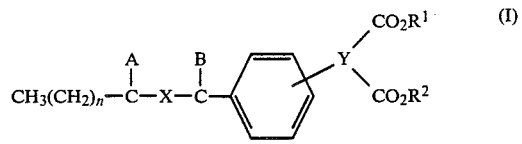

or a salt thereof, in which
Y is a group —O(CH$_2$)$_m$CH<, —(CH$_2$)$_m$CH<, or —CH=C< where
  m is an integer of from 1 to 5,
  n is an integer of from 4 to 12,
  each of R$^1$ and R$^2$, which may be the same or different, represents hydrogen or C$_{1-6}$ alkyl,
X represents a double or triple bond, and each of A and B represents hydrogen when X is a double bond, or both A and B are absent when X is a triple bond.

2. A compound according to claim 1, in which the substituents on the aromatic ring are in the 1,2- or 1,3-position.

3. A compound according to claim 1 in which n is an integer from 8 to 12.

4. A compound according to claim 1, in which m is 1, 2 or 3.

5. A compound according to claim 1 in which, when X is a double bond, the hydrocarbon chain containing X has the (Z) absolute configuration.

6. A compound according to claim 1 selected from
2-[2-(1-tridecynyl)phenyl]methylenepropan-1,3-dioic acid mono ethyl ester;
2-[2-(1-tridecynyl)phenyl]methylenepropan-1,3-dioic acid;
2-[2-(1-tridecynyl)phenyl]methylpropan-1,3-dioic acid;
2-[2-[(Z)-1-tridecenyl]phenyl]methylenepropan-1,3-dioic acid;
2-[3-(1-tridecynyl)phenyl]methylenepropan-1,3-dioic acid;
2-[3-(1-tridecynyl)phenyl]methylpropan-1,3-dioic acid;
2-[3-[2-(1-octynyl)phenoxy]propyl]propan-1,3-dioic acid mono ethyl ester;
2-[3-[3-(1-octynyl)phenoxy]propyl]propan-1,3-dioic acid mono ethylester;
2-[3-[2-(1-octynyl)phenoxy]propyl]propan-1,3-dioic acid;
2-[3-[3-(1-octynyl)phenoxy]propyl]propan-1,3-dioic acid;
2-[3-[(Z)-1-tridecenyl]phenyl]methylenepropan-1,3-dioic acid;
2-[3-[(Z)-1-tridecenyl]phenyl]methylpropan-1,3-dioic acid;
2-[3-[3-[Z]-1-octenyl)phenoxy]-propyl]propan-1,3-dioic acid mono ethyl ester;
2-[3-[3-[Z]-1-octenyl)phenoxy]propyl]propan-1,3-dioic acid.

7. A pharmaceutical composition comprising a compound of formula (I):

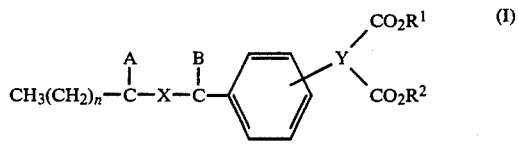

or a pharmaceutically acceptable salt thereof, in which
Y is a group $-O(CH_2)_mCH<$, $-(CH_2)_mCH<$, or $-CH=C<$ where
m is an integer of from 1 to 5,
n is an integer of from 4 to 12,
each of $R^1$ and $R^2$, which may be the same or different, represents hydrogen or $C_{1-6}$ alkyl,
X represents a double or triple bond, and each of A and B represents hydrogen when X is a double bond, or both A and B are absent when X is a triple bond; and a pharmaceutically acceptable carrier.

8. A method for treating allergic diseases in a human or non-human animal which comprises administering to the animal an effective, non-toxic amount of a compound of formula (I):

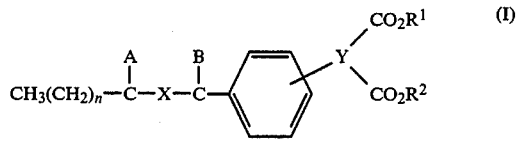

or a pharmaceutically acceptable salt thereof, in which
Y is a group $-(CH_2)_mCH<$, $-(CH_2)_mCH<$, or $-CH=C<$ where
m is an integer of from 1 to 5,
n is an integer of from 4 to 12,
each of $R^1$ and $R^2$, which may be the same or different, represents hydrogen or $C_{1-6}$ alkyl,
, X represents a double or triple bond, and each of A and B represents hydrogen when X is a double bond, or both A and B are absent when X is a triple bond.

* * * * *

UNITED STATES PATENT AND TRADEMARK OFFICE
CERTIFICATE OF CORRECTION

PATENT NO. : 4,699,995

DATED : October 13, 1987

INVENTOR(S) : Derek Richard Buckle

It is certified that error appears in the above-identified patent and that said Letters Patent is hereby corrected as shown below:

In claim 6 at column 25, line 37, before "[Z]", kindly insert --(--; and at line 39, before "[Z]", kindly insert --(--.

Signed and Sealed this

Sixteenth Day of February, 1988

*Attest:*

DONALD J. QUIGG

*Attesting Officer*  *Commissioner of Patents and Trademarks*